US011192945B2

(12) United States Patent
Edwards et al.

(10) Patent No.: US 11,192,945 B2
(45) Date of Patent: Dec. 7, 2021

(54) ANTI-TGF-β INDUCTION OF BONE CELL FUNCTION AND BONE GROWTH

(71) Applicants: Vanderbilt University, Nashville, TN (US); Vanderbilt University, Nashville, TN (US)

(72) Inventors: James R. Edwards, Oxford (GB); Gregory R. Mundy

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 14/582,631

(22) Filed: Dec. 24, 2014

(65) Prior Publication Data

US 2015/0183862 A1   Jul. 2, 2015

Related U.S. Application Data

(63) Continuation of application No. 13/266,082, filed as application No. PCT/US2010/032373 on Apr. 26, 2010, now abandoned.

(60) Provisional application No. 61/172,539, filed on Apr. 24, 2009.

(51) Int. Cl.
| | |
|---|---|
| *A61K 39/395* | (2006.01) |
| *C07K 16/22* | (2006.01) |
| *A61P 19/08* | (2006.01) |
| *A61P 19/10* | (2006.01) |
| *C07K 16/24* | (2006.01) |
| *A61K 39/00* | (2006.01) |

(52) U.S. Cl.
CPC .......... *C07K 16/24* (2013.01); *A61K 39/3955* (2013.01); *A61P 19/08* (2018.01); *A61P 19/10* (2018.01); *C07K 16/22* (2013.01); *A61K 2039/505* (2013.01); *A61K 2039/545* (2013.01); *C07K 2317/76* (2013.01)

(58) Field of Classification Search
CPC .... A61K 39/3955; A61K 19/08; A61K 19/10; C07K 16/22
See application file for complete search history.

(56) References Cited

U.S. PATENT DOCUMENTS

| | | | | | |
|---|---|---|---|---|---|
| 5,919,808 | A | * | 7/1999 | Petrie | A61K 31/196 514/369 |
| 7,527,791 | B2 | * | 5/2009 | Adams | C07K 16/22 424/130.1 |
| 2003/0125251 | A1 | | 7/2003 | Wakefield et al. | |
| 2005/0158307 | A1 | * | 7/2005 | Spies | C07K 16/2851 424/141.1 |
| 2005/0208027 | A1 | * | 9/2005 | Conboy | A61K 38/1709 424/93.7 |
| 2005/0276802 | A1 | * | 12/2005 | Adams | C07K 16/22 424/141.1 |
| 2006/0015952 | A1 | * | 1/2006 | Filvaroff | A01K 67/0271 800/10 |
| 2006/0057145 | A1 | | 3/2006 | Berzofsky et al. | |
| 2006/0089723 | A1 | * | 4/2006 | Murphy | A61B 17/58 623/23.62 |
| 2009/0035304 | A1 | * | 2/2009 | Khanna | A61K 38/13 424/133.1 |
| 2010/0003256 | A1 | * | 1/2010 | Lu | C07K 14/495 424/139.1 |

FOREIGN PATENT DOCUMENTS

| | | |
|---|---|---|
| WO | WO 1996-022790 | 8/1996 |
| WO | WO 2007-076391 | 7/2007 |

OTHER PUBLICATIONS

Miyakoshi et al., Arch. Orthop. Trauma Surg., 2005, vol. 125:683-692.*
Magrey et al., Curr. Rheumatol. Rep., 2010, vol. 12:332-336.*
Takata et al., J. Med. Invest., 2001, vol. 48:147-156.*
Ajala et al., Endocrine Abstracts, Mar. 2009, vol. 19:p. 19.*
Cummings et al., Lancet, 2002, vol. 359:1761-1767.*
Dumont et al., Cancer Cell, 2003, vol. 3(6):531-536.*
Alliston et al., "TGF-beta-induced repression of CBFA1 by Smad3 decreases cbfa1 and osteocalcin expression and inhibits osteoblast differentiation," The EMBO Journal, 20(9):2254-2272,2001.
Biswas et al., "Anti-transforming growth factor beta antibody treatment rescues bone loss and prevents breast cancer metastasis to bone," PLoS One, 6(1 1):e27090, 2011.
Biswas et al., "Doxorubicin therapy causes additional bone loss in preclinical osteolytic breast cancer model," Bone, 46:S35, 2010.
Edwards et al., "Inhibition of TGF-beta signaling by 1D11 antibody treatment increases bone mass and quality in vivo," Journal of Bone and Mineral Research, 25(11):2419-2426, 2010.
Edwards et al., "TGF-beta blockade by 1D11 antibody treatment improves bone volume, strength and micro-structural properties in vivo," Bone, 47:S64, 2010.
Extended European Search Report issued in European Application No. 10767880.7, dated Dec. 21, 2012.
Filvaroff et al., "Inhibition of TGF-beta receptor signaling in osteoblasts leads to decreased bone remodeling and increased trabecular bone mass," *Development*, 126(19):4267-4279, 1999.
Frazier et al., "Comparison of craniofacial phenotype in craniosynostotic rabbits treated with anti-TGF-beta2 at suturectomy site," *The Cleft Palate-Craniofacial Journal*, 45(6):571-582, 2008.
Ganapathy et al., "Targeting the transforming growth factor-I pathway inhibits human basal-like breast cancer metastasis," *Molecular Cancer*, 9(1): 122, 2010.
Itoh et al., "Importance of membrane- or matrix-associated forms of M-CSF and RANKL/ODF in osteoclastogenesis supported by SaOS-4/3 cells expressing recombinant PTH/PTHrP receptors," *Journal of Bone and Mineral Research*, 15(9): 1766-1775, 2000.

(Continued)

*Primary Examiner* — Xiaozhen Xie
(74) *Attorney, Agent, or Firm* — Parker Highlander PLLC

(57) ABSTRACT

The invention regards the modulation of TGF-β activity by administering to a subject an antibody that binds to TGF-β, thereby increasing bone growth, bone formation, bone mass and bone strength. The antibody acts to increase osteoblast number and function while at the same time decreasing osteoclast number and function. Such drugs are useful in the treatment of diseases or disorders such as osteoporosis, Paget's disease, metastatic bone cancer, myeloma bone disease, bone fractures, etc.

7 Claims, 5 Drawing Sheets

(56) References Cited

OTHER PUBLICATIONS

Kang et al., "Repression of Runx2 function by TGF-beta through recruitment of class II histone deacetylases by Smad3," *The EMBO Journal*, 24(14):2543-2555, 2005.

Lee and Lorenzo, "Parathyroid hormone stimulates TRANCE and inhibits osteoprotegerin messenger ribonucleic acid expression in murine bone marrow cultures: correlation with osteoclast-like cell formation," *Endocrinology*, 140(8):3552-3561, 1999.

Mohammad et al., "Pharmacologic inhibition of the TGF-beta type I receptor kinase has anabolic and anti-catabolic effects on bone," *PLoS One*, 4:e5275, 2009.

Mooney et al., "Anti-TGF-β2 antibody therapy inhibits postoperative resynostosis in cranio synostotic rabbits," *Plastic and Reconstructive Surgery*, 119(4): 1200-1215, 2007.

Mooney et al., "Postoperative anti-TGF-β2 antibody therapy improves intracranial volume and craniofacial growth in craniosynostotic rabbits," *The Journal of Craniofacial Surgery*, 18(2):336-349, 2007.

Office Action, issued in Japanese Application No. 2012-507465, dated May 28, 2014. (English Translation).

Office Action, issued in U.S. Appl. No. 13/266,082, dated Jun. 10, 2013.

Office Action, issued in U.S. Appl. No. 13/266,082, dated Nov. 6, 2013.

Office Action, issued in U.S. Appl. No. 13/266,082, dated Jul. 24, 2014.

Opperman et al., "Cranial suture obliteration is induced by removal of transforming growth factor (TGF)-β 3 activity and prevented by removal of TGF-β 2 activity from fetal rat calvaria in vitro," *Journal of Craniofacial Genetics and Developmental Biology*, 19(3): 164-173, 1999.

PCT International Preliminary Report on Patentability issued in International Application No. PCT/US2010/032373, dated Nov. 3, 2011.

PCT International Search Report and Written Opinion issued in International Application No. PCT/US2010/032373, dated Dec. 15, 2010.

Quinn et al. "Transforming growth factor beta affects osteoclast differentiation via direct and indirect actions," *Journal of Bone and Mineral Research*, 16:1787-94, 2001.

Raisz, "Pathogenesis of osteoporosis: concepts, conflicts, and prospects," *Journal of Clinical Investigation*, 115(12):3318-3325, 2005.

Thirunavukkarasu et al., "Stimulation of osteoprotegerin (OPG) gene expression by transforming growth factor-beta (TGF-beta). Mapping of the OPG promoter region that mediates TGF-beta effects," *Journal of Biological Chemistry*, 276:36241-50, 2001.

Partial European Search Report issued in European Application No. 16180079.2, dated Jan. 27, 2017.

Stebbins et al., "Inhibition of TGFβ signaling enhances bone mass by increasing osteoblast and reducing osteoclast number and activity," *Journal of Bone and Mineral Research*, 20(S1):S63, 2006.

* cited by examiner

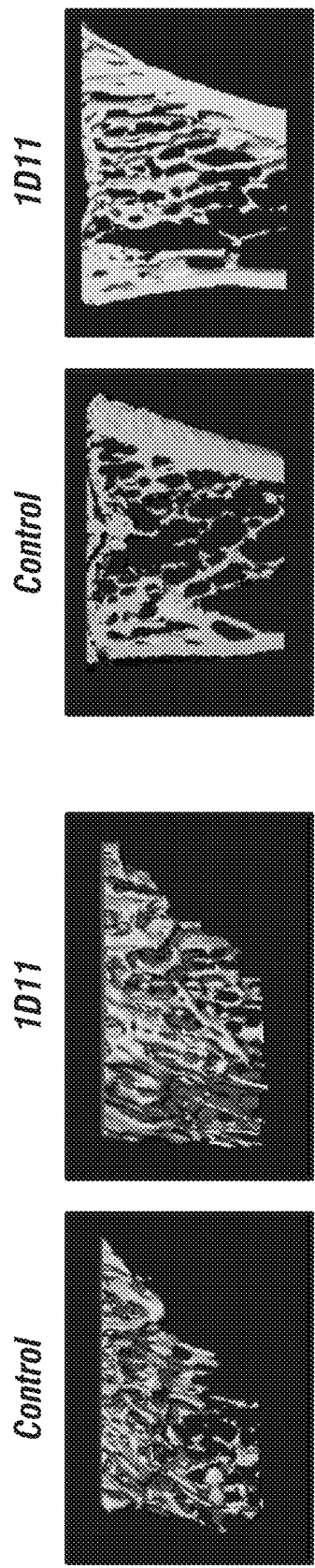
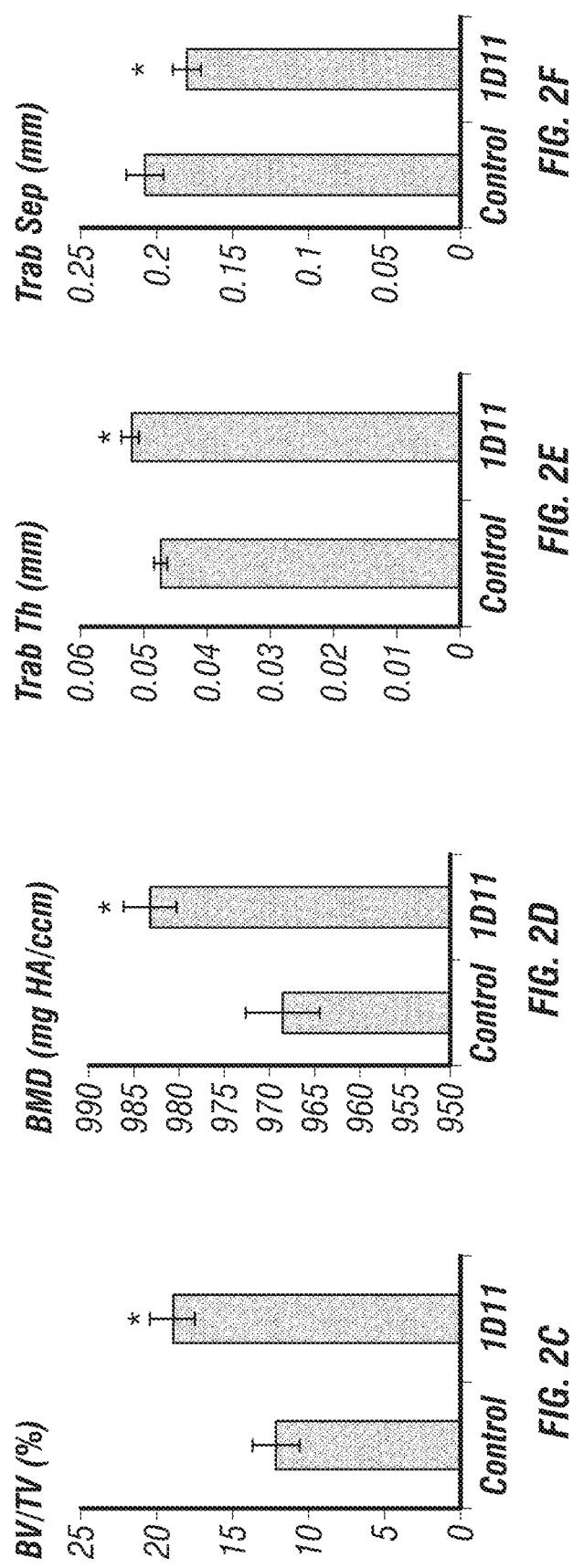
FIG. 2A
FIG. 2B
FIG. 2C
FIG. 2D
FIG. 2E
FIG. 2F

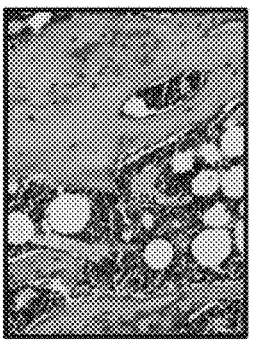
FIG. 4A
FIG. 4B
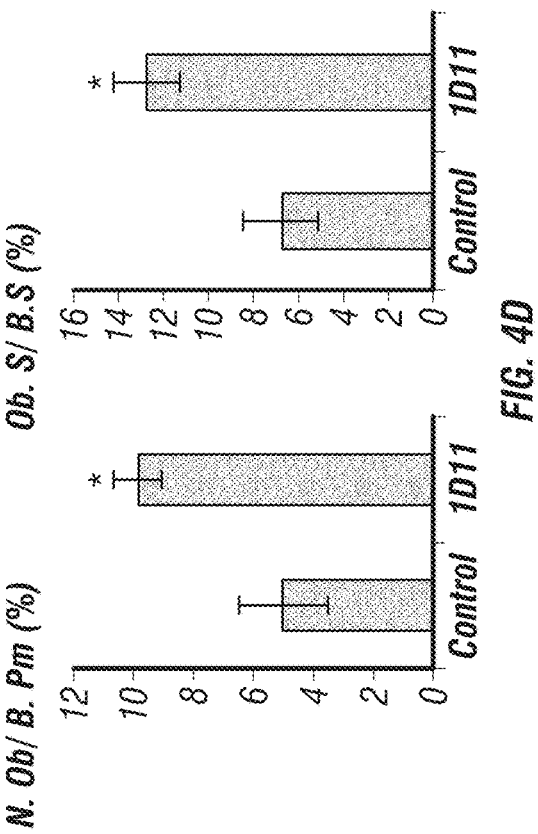
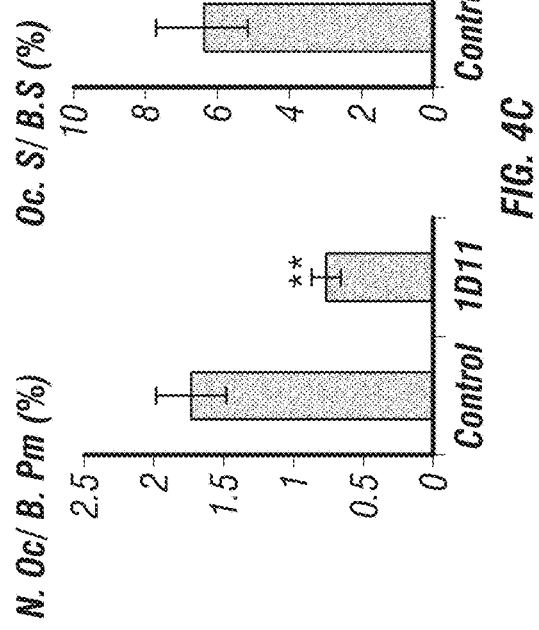
FIG. 4C
FIG. 4D

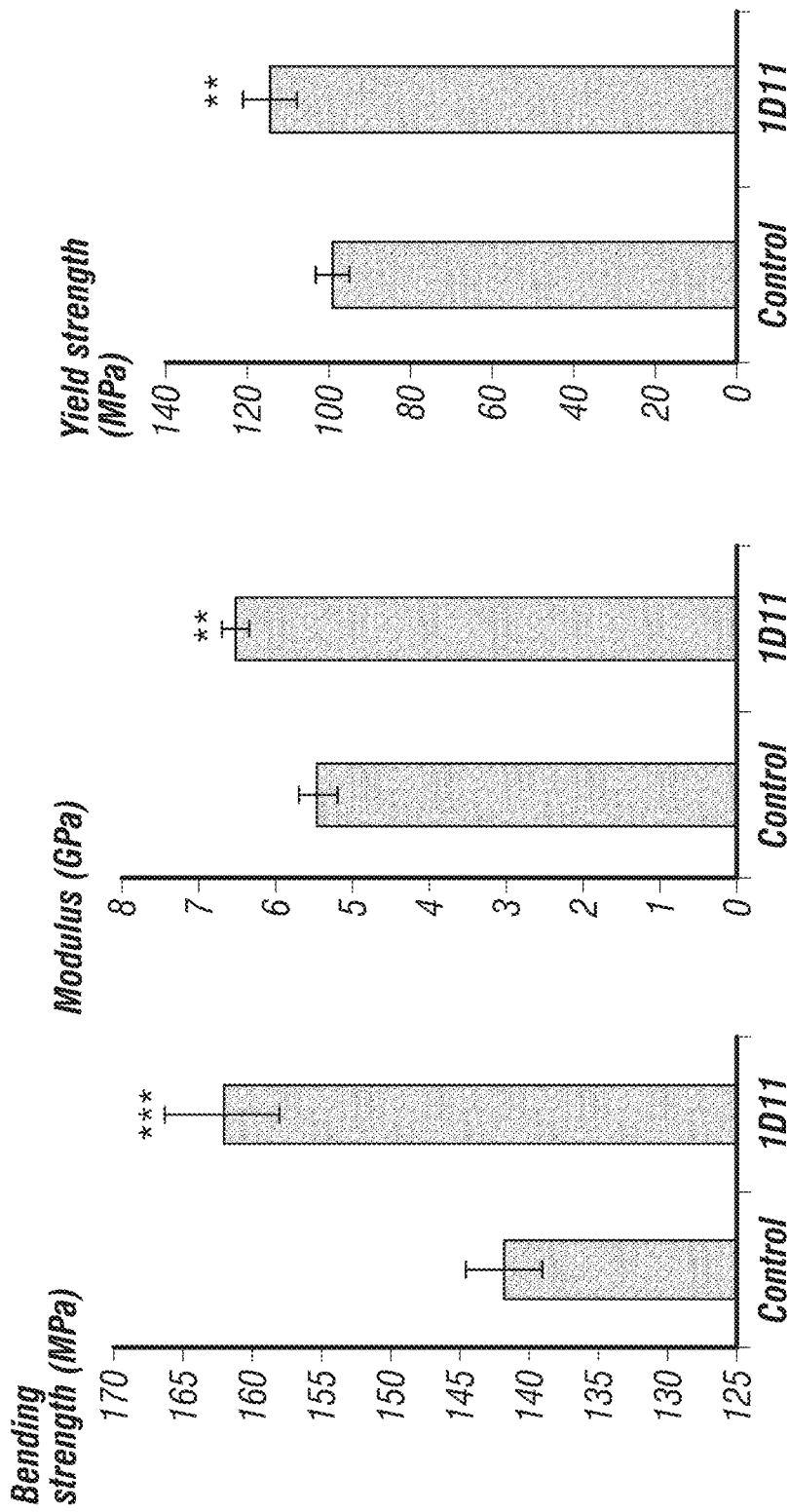

ANTI-TGF-β INDUCTION OF BONE CELL FUNCTION AND BONE GROWTH

This present application is a continuation of U.S. application Ser. No. 13/266,082, filed Jun. 25, 2012, now abandoned, which is a national phase application under 35 U.S.C. § 371 of International Patent Application No. PCT/US2010/032373, filed Apr. 26, 2010, which claims benefit of priority to U.S. Provisional Application No. 61/172,539, filed Apr. 24, 2009, the entire contents of each of which being hereby incorporated by reference.

Monoclonal antibody 1D11 (IgG1) refers to the mAb produced by a clone of the murine hybridoma cell line 1D11. Samples of this cell line were deposited on Oct. 7, 1988 with the American Type Culture Collection (ATCC), 12301 Parklawn Drive, Rockville, Md. Cell line 1D11.16 and assigned ATCC HB9849, the publicly availability of which is guaranteed for thirty years after the issue date of this patent.

BACKGROUND OF THE INVENTION

I. Field of the Invention

The present invention relates to the fields of molecular biology and medicine. More particularly, it relates to the fields of bone disease & injury, bone repair, bone implants, bone grafts, periodontal disease and cancer. Specifically, it deals with the use of anti-TGF-β antibodies to promote bone growth and formation, to increase bone mass and strength, and thereby to treat bone diseases such as osteoporosis, as well as bone trauma and cancers with bone involvement, including multiple myeloma and myeloma bone disease.

II. Related Art

Over 200 million people worldwide suffer from bone disorders such as osteoporosis, bone fractures, and periodontal (gum) disease (where the teeth loose surrounding bone). Osteoporosis represents a large and rapidly growing health care problem with an unmet medical need for therapies that stimulate bone formation. Most current drugs for osteoporosis retard bone degradation but do not stimulate bone formation to replace already lost bone. Compounds that stimulate bone formation thus represent an unmet need in the area of bone disease. Osteoporosis is known to affect approximately 100 million people worldwide—35 million of whom live in the U.S., Western Europe and Japan. Moreover, over 25 million individuals suffer bone fractures yearly, 60 million have periodontal disease (in which the tooth loosens from the jaw bone), and another 18 million have other bone disorders such as bone cancer.

Most current therapies for osteoporosis patients focus on prevention of bone loss, not bone formation. This remains an important consideration as significant morbidity and mortality are associated with prolonged bed rest in the elderly that occurs post bone fracture, particularly those who have suffered hip fractures. Complications of bed rest include blood clots and pneumonia. These complications are recognized and measures are usually taken to avoid them, but these are hardly the best approach to therapy.

Yet another bone-related health issues is bone reconstruction and, specifically, the ability to reconstruct defects in bone tissue that result from traumatic injury, as a consequence of cancer or cancer surgery, as a result of a birth defect, or as a result of aging. There is a significant need for more frequent orthopedic implants, and cranial and facial bone are particular targets for this type of reconstructive need. The availability of new implant materials, e.g., titanium, has permitted the repair of relatively large defects. Titanium implants provide excellent temporary stability across bony defects. However, experience has shown that a lack of viable bone bridging the defect can result in exposure of the appliance, infection, structural instability and, ultimately, failure to repair the defect.

Autologous bone grafts are another possibility to deal with bone injury, but they have several demonstrated disadvantages in that they must be harvested from a donor site such as iliac crest or rib, they usually provide insufficient bone to completely fill the defect, and the bone that does form is sometimes prone to infection and resorption. Partially purified xenogeneic preparations are not practical for clinical use because microgram quantities are purified from kilograms of bovine bone, making large scale commercial production both costly and impractical. Allografts and demineralized bone preparations are therefore often employed. Microsurgical transfers of free bone grafts with attached soft tissue and blood vessels can close bony defects and allow an immediate source of blood supply to the graft. However, these techniques are time consuming, have been shown to produce a great deal of morbidity, and can only be used by specially trained individuals.

Another form of bone disease is that resulting from cancer. A number of cancers metastasize to bone and can result in bone weakening, and some are even associated with bone destruction and bone loss, such as breast, lung, thyroid, kidney and prostate cancer. In addition, Multiple Myeloma and its associated myeloma bone disease (MBD) is not a metastatic cancer. Rather, myeloma cells are derived from the B-cells of the immune system that normally reside in the bone marrow and are therefore intimately associated with bone. Indeed, the bone marrow microenvironment plays an important role in the growth, survival and resistance to chemotherapy of the myeloma cells, which, in turn, regulate the increased bone loss associated with this disorder (world-wide-web at multiplemyeloma.org). Over 90% of myeloma patients have bone involvement, versus 40-60% of cancer patients who have bone metastasis, and over 80% of these MBD patients have intractable bone pain. Additionally, approximately 30% of myeloma patients have hypercalcemia that is a result of the increased osteolytic activity associated with this disease (Cavo et al., 2006).

Unlike the osteolysis associated with other bone tumors, the MBD lesions are unique in that they do not heal or repair, despite the patients' having many years of complete remission (world-wide-web at multiplemyeloma.org; Terpos et al., 2005). Mechanistically, this seems to be related to the inhibition and/or loss of the bone-forming osteoblast during disease progression. Indeed, bone marker studies and histomorphometry indicate that both the bone-resorbing osteoclast and osteoblast activity are increased, but balanced early in the disease, whereas overt MBD shows high osteoclast activity and low osteoblast activity (world-wide-web at multiplemyeloma.org). Thus, MBD is a disorder in which bone formation and bone loss are uncoupled and would benefit from therapies that both stimulate bone formation and retard its loss. To date, no such therapies exist. Therefore, there continues to be a need for improved methods of stimulating bone formation and increasing bone strength in vivo to treat bone disease and injury, including cancer.

SUMMARY OF THE INVENTION

Thus, in accordance with the present invention, there is provided a method of increasing bone mass and/or volume in a subject comprising (a) identifying a patient in need of increased bone mass and/or volume; and (b) administering to said subject an antibody that binds immunologically the TGF-β. The antibody may bind all three isoforms of TGF-β. The antibody may be designated as 1D11, and may be a humanized version of 1D11, or any engineered version containing the CDRs of 1D11 in a heterologous framework.

In one embodiment, the antibody is such that it specifically binds to at least one isoform of TGF-β. In particular embodiments, the anti-TGF-β antibody specifically binds at least one isoform of TGF-β selected from the group consisting of TGF-β1, TGF-β2, and TGF-β3. In yet other embodiments, the anti-TGF-β antibody specifically binds to at least: (a) TGF-β1, TGF-β2, and TGF-β3 (also referred to as "pan-neutralizing antibody"); (b) TGF-β1 and TGF-β2; (c) TGF-β1 and TGF-β3; and (d) TGF-β2 and TGF-β3. In various embodiments, the affinity constant Ka of the TGF-β antibody for at least one isoform of TGF-b, which it specifically binds, is preferably greater than $10^6$ M$^{-1}$, $10^7$ M$^{-1}$, $10^8$ M$^{-1}$, $10^9$ M$^{-1}$, $10^{10}$ M$^{-1}$, $10^{11}$ M$^{-1}$, or $10^{12}$ M$^{-1}$. In yet further embodiments, the antibody of the invention specifically binds to a protein substantially identical to human TGF-β1, TGF-β2, and/or TGF-β3. Also contemplated for use in humans are chimeric and humanized forms and derivatives of nonhuman antibodies. Producing such variants is well within the ordinary skill of an artisan (see, e.g., Antibody Engineering, ed. Borrebaeck, 2nd ed., Oxford University Press, 1995).

In one embodiment, the anti-TGF-β antibody is a murine monoclonal antibody 1D11 produced by the hybridoma 1D11.16 (ATCC Deposit Designation No. HB 9849, also described in U.S. Pat. Nos. 5,571,714, 5,772,998 and 5,783, 185). The 1D11 antibody specifically binds all three mammalian isoforms of TGF-β. The sequence of the 1D11 heavy chain variable region is available under Accession No. AAB46787. In related embodiments, the anti-TGF-β antibody is a derivative of 1D11, e.g., an antibody comprising the CDR sequences identical to those in 1D11 (e.g., a chimeric, humanized or CDR-grafted antibody). In yet a further embodiment, the anti-TGF-β antibody is a fully human recombinant antibody.

The antibody may be administered to said subject systemically, intravenously, intra-peritoneally, intramuscularly, subcutaneously or topically. The antibody may be administered to a bone target site, including injection at the site. The antibody also may be comprised in a time-release device implanted at the site.

The subject may be a human or a non-human animal, such as a mouse, a rat, a rabbit, a dog, a cat, a horse, a monkey or a cow. The subject may have cancer, or may not. The method may further comprise at least a second administration of said antibody, including regimens of three administrations per week. The subject may receive at least 9 administrations. The subject may suffer from osteoporosis, bone fracture, bone loss due to trauma, or Paget's Disease, or from bone loss due to cancer metastasis. The method may further comprise assessing bone mass following administration of said antibody, such as by bone imaging.

In another embodiment, there is provided a method of increasing bone growth in a subject comprising administering to said subject an antibody that binds immunologically the TGF-β. The antibody may bind all three isoforms of TGF-β. The antibody may be designated as 1D11, and may be a humanized version of 1D11, or any engineered version containing the CDRs of 1D11 in a heterologous framework. The antibody may be administered to said subject systemically, intravenously, intra-peritoneally, intramuscularly, subcutaneously or topically. The antibody may be administered to a bone target site, including injection at the site. The antibody also may be comprised in a time-release device implanted at the site. The subject may be a human or a non-human animal, such as a mouse, a rat, a rabbit, a dog, a cat, a horse, a monkey or a cow. The subject may have cancer, or may not.

In other embodiments, there are provided:
a method of increasing osteoblast number in a subject comprising administering to said subject an antibody that binds immunologically the TGF-β;
a method of decreasing osteoclast number in a subject comprising administering to said subject an antibody that binds immunologically the TGF-β;
a method of increasing bone strength in a subject comprising administering to said subject an antibody that binds immunologically the TGF-β; and
a method of decreasing TGF-β signaling in a subject comprising administering to said subject an antibody that binds immunologically the TGF-β.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error for the device, the method being employed to determine the value, or the variation that exists among the study subjects.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A-F—1D11 treatment increases bone volume. 3-dimensional rendered images from μCT scanned regions of tibial metaphysis (200 μm) showed increased bone volume in 1D11-treated mice (FIGS. 2A-B), accompanied by an increased BV/TV (FIG. 2C) and BMD (FIG. 2D). A thickening of trabeculae (FIG. 2E), and decreased trabecular spacing was also observed within this region in 1D11-treated animals (FIG. 2F; *=p<0.05).

FIGS. 4A-D—Cellular distribution of bone cells following 1D11 treatment. Decalcified tibial sections stained for TRAP showed a considerable decrease in positively-stained osteoclasts lining the trabecular bone surface in treated animals compared to controls (FIG. 4A, original mag ×4; FIG. 4B, original mag ×20; black arrows=osteoclasts). Cellular distribution was quantified by histomorphometric analysis of H&E- and TRAP-stained sections, and demonstrated a significant decrease in osteoclast number and surface on the bone of 1D11-treated mice (FIG. 4C, **$p<0.01$). Osteoblast numbers were significantly elevated in mice treated with the 1D11 antibody (FIG. 4D, *$p<0.05$).

FIGS. 5A-C Biomechanical testing. Fresh dissected femurs isolated from 1D11 treated or control mice were examined biomechanically by 3-point bending. Femurs were positioned horizontally and monotonically loaded at a rate of 3 mm/min at the mid-diaphysis. 1D11 treatment significantly increased bending strength (FIG. 5A), yield strength (FIG. 5C) and tissue modulus (FIG. 5B) (=$p<0.01$; *=$p<0.001$).

DETAILED DESCRIPTION OF THE INVENTION

Figure 1:
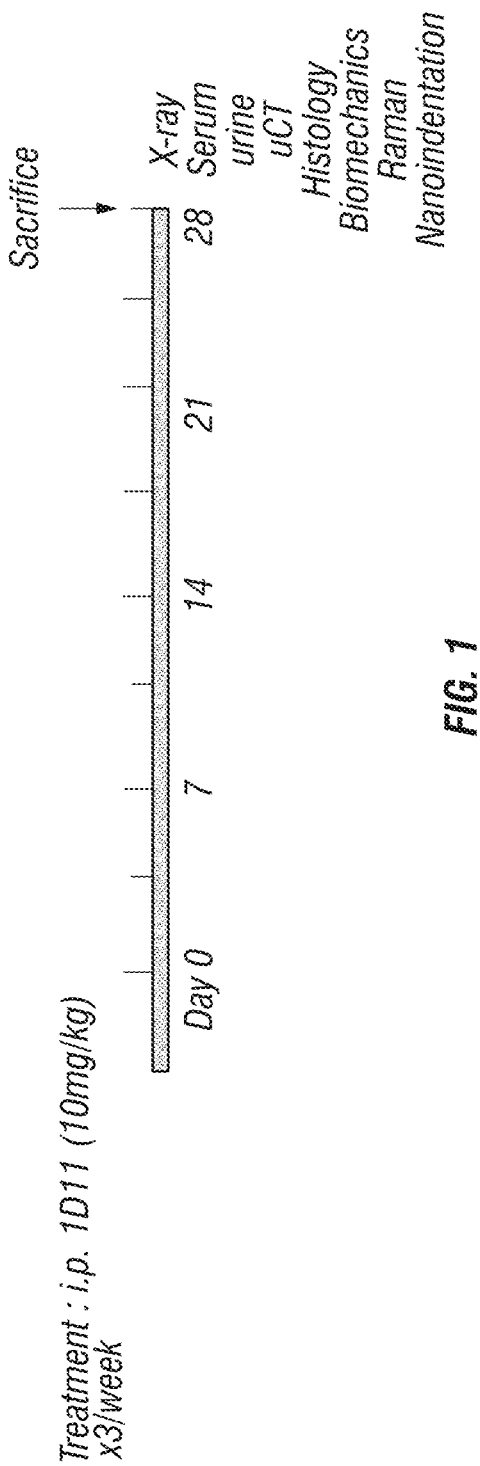
FIG. 1—Treatment regimen. C57Bl/6 mice (n=5) were treated i.p. with 1D11 or control antibody (13C4) 3 times/week for 28 days. Skeletal parameters were determined by μCT scanning, histomorphometric analysis and biochemical testing. Effects of anti-TGF-β therapy on cell distribution and gene/protein expression were also determined.

TGF-β is an abundant bone matrix protein which influences the formation, function and cell-cell interactions of osteoblasts and osteoclasts, to control bone remodeling and maintain adequate bone mass. As such, the TGF-β signaling pathway represents a unique pharmacological target, with the potential to regulate bone volume and quality through the control of both osteoblasts and osteoclasts. Previous studies using murine models containing genetic modifications in the TGF-β signaling pathway have shown that reduced TGF-β signaling enhances the mechanical properties and mineral concentration of the bone matrix, as well as bone mass. Although small molecule inhibitors of TGF-β signaling have been shown to decrease cancer growth and invasiveness, the direct effect of TGF-β blockade on the normal bone marrow environment in non-tumor bearing mice has not been fully addressed.

Therefore, the inventors examined the ability of an anti-TGF-β antibody to block TGF-β signaling pathways. This antibody positively regulated osteoblast numbers while simultaneously decreasing the amount of active osteoclasts in the marrow. This resulted in a profound increase in bone volume and quality. These findings clearly illustrate the potential of compounds which can specifically target the TGF-β signaling pathway in vivo, and suggest a therapeutic approach to increase bone mass and strength. These and other aspects of the invention are set forth in detail below.

I. ANTI-TGF-β

A. TGF-β

Transforming growth factor β (TGF-β) controls proliferation, cellular differentiation, and other functions in most cells. It plays a role in immunity, cancer, heart disease, diabetes, and Marfan syndrome. TGF-β acts as an antiproliferative factor in normal epithelial cells and at early stages of oncogenesis. Some cells secrete TGF-β, and also have receptors for TGF-β. This is known as autocrine signalling. Cancerous cells increase their production of TGF-β, which also acts on surrounding cells.

TGF-β is a secreted protein that exists in three isoforms called TGF-β1, TGF-β2 and TGF-β3. It was also the original name for TGF-β1, which was the founding member of this family. The TGF-β family is part of a superfamily of proteins known as the transforming growth factor beta superfamily, which includes inhibins, activin, anti-mullerian hormone, bone morphogenetic protein, decapentaplegic and Vg-1.

The peptide structures of the three members of the TGF-β family are highly similar. They are all encoded as large protein precursors; TGF-β1 contains 390 amino acids and TGF-β2 and TGF-β3 each contain 412 amino acids. They each have an N-terminal signal peptide of 20-30 amino acids that they require for secretion from a cell, a pro-region (called latency associated peptide or LAP), and a 112-114 amino acid C-terminal region that becomes the mature TGF-β molecule following its release from the pro-region by proteolytic cleavage. The mature TGF-β protein dimerizes to produce a 25 KDa active molecule with many conserved structural motifs. TGF-β has nine cysteine residues that are conserved among its family; eight form disulfide bonds within the molecule to create a cysteine knot structure characteristic of the TGF-β superfamily while the ninth cysteine forms a bond with the ninth cysteine of another TGF-β molecule to produce the dimer. Many other conserved residues in TGF-β are thought to form secondary structure through hydrophobic interactions. The region between the fifth and sixth conserved cysteines houses the most divergent area of TGF-β molecules that is exposed at the surface of the molecule and is implicated in receptor binding and specificity of TGF-β.

TGF-β induces apoptosis in numerous cell types. TGF-β can induce apoptosis in two ways: through the SMAD pathway or the DAXX pathway. The SMAD pathway is the canonical signaling pathway that TGF-β family members signal through. In this pathway, TGF-β dimers bind to a type II receptor which recruits and phosphorylates a type I receptor. The type I receptor then recruits and phosphorylates a receptor regulated SMAD (R-SMAD). SMAD3, an R-SMAD, has been implicated in inducing apoptosis. The R-SMAD then binds to the common SMAD (coSMAD) SMAD4 and forms a heterodimeric complex. This complex then enters the cell nucleus where it acts as a transcription factor for various genes, including those to activate the mitogen-activated protein kinase 8 pathway, which triggers apoptosis. TGF-β may also trigger apoptosis via the death associated protein 6 (DAXX adapter protein). DAXX has been shown to associate with and bind to the type II TGF-β receptor kinase. TGF-β is believed to be important in regulation of the immune system by CD25+ regulatory. TGF-β appears to block the activation of lymphocytes and monocyte derived phagocytes.

B. Antibodies

Production Methods.

In another aspect, the present invention contemplates an antibody that is immunoreactive with TGF-β, including being cross-reactive with TGF-β isoforms 1-3. The antibody can be a monoclonal antibody, but use of a polyclonal antibody preparation with the same TGF-β1-3 specificity could be employed. Means for preparing and characterizing antibodies are well known in the art (see, e.g., Harlow and Lane, 1988).

Briefly, polyclonal antibodies are prepared by immunizing an animal with an immunogen (i.e., TGF-β or a fragment thereof) and collecting antisera from that immunized animal. A wide range of animal species can be used for the production of antisera. Typically, an animal used for production of antisera is a non-human animal including rabbits, mice, rats, hamsters, pigs or horses. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, i.e., a purified or partially purified TGF-β protein, polypeptide or peptide or cell expressing high levels of TGF-β. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al. (1977). The use of electrically induced fusion methods is also appropriate (Goding, 1986).

Fusion procedures usually produce viable hybrids at low frequencies, around $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

Modified Antibodies.

In one embodiment, antibody molecules will comprise fragments (such as (F(ab'), F(ab')2) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

It may desirable to "humanize" antibodies produced in non-human hosts in order to attenuate any immune reaction when used in human therapy. Such humanized antibodies may be studied in an in vitro or an in vivo context. Humanized antibodies may be produced, for example by replacing an immunogenic portion of an antibody with a corresponding, but non-immunogenic portion (i.e., chimeric antibodies). PCT Application PCT/US86/02269; EP Application 184,187; EP Application 171,496; EP Application 173,494; PCT Application WO 86/01533; EP Application 125,023; Sun et al. (1987); Wood et al. (1985); and Shaw et al. (1988); all of which references are incorporated herein by reference. General reviews of "humanized" chimeric antibodies are provided by Morrison (1985; also incorporated herein by reference. "Humanized" antibodies can alternatively be produced by CDR or CEA substitution. Jones et al. (1986); Verhoeyan et al. (1988); Beidler et al. (1988); all of which are incorporated herein by reference.

In more specific embodiments, one may use the CDR regions from antibody 1D11 and place these into the framework regions of any other suitable antibody, human or non-human. The anti-TGF-β antibody 1D11 is a murine monoclonal antibody produced by the hybridoma 1D11.16 (ATCC Deposit Designation No. HB 9849, also described in U.S. Pat. Nos. 5,571,714, 5,772,998 and 5,783,185, incorporated by reference herein). The 1D11 antibody specifically binds all three mammalian isoforms of TGF-β. The sequence of the 1D11 heavy chain variable region is available under Accession No. AAB46787.

In related embodiments, the anti-TGF-β antibody is a derivative of 1D11, e.g., an antibody comprising the CDR sequences identical to those in 1D11 (e.g., a chimeric, humanized or CDR-grafted antibody). In yet a further embodiment, the anti-TGF-β antibody is a fully human recombinant antibody.

II. BONE STRUCTURE AND PHYSIOLOGY

Bone is a living, growing tissue. It is porous and mineralized, and made up of cells, vessels, organic matrix and inorganic hydroxyapatite crystals. The human skeleton is actually made up of 2 types of bones: the cortical bone and the trabecular bone. Cortical bone represents nearly 80% of the skeletal mass. Cortical bone has a slow turnover rate and a high resistance to bending and torsion. It provides strength where bending would be undesirable as in the middle of long bones. Trabecular bone only represents 20% of the skeletal mass, but 80% of the bone surface. It is less dense, more elastic and has a higher turnover rate than cortical bone.

A. Bone Forming Cells

Osteoprogenitors.

Human bone precursor cells are characterized as small-sized cells that express low amounts of bone proteins (osteocalcin, osteonectin, and alkaline phosphatase) and have a low degree of internal complexity (Long et al., 1995). When stimulated to differentiate, these preosteoblast cells become osteoblast in their appearance, size, antigenic expression, and internal structure. Although these cells are normally present at very low frequencies in bone marrow, a process for isolating these cells has been described (Long et al., 1995). U.S. Pat. No. 5,972,703 further describes methods of isolating and using bone precursor cells, and is specifically incorporated herein by reference.

A number of studies indicate that bone marrow derived cells have osteogenic potential. The majority of these investigations point to mesenchymal stem cells (MSC) as undergoing differentiation into osteoblasts when cultured in the presence of bone-active cytokines (Jaiswal et al., 2000; Phinney et al., 1999; Aubin, 1998; Zohar et al., 1997). Mesenchymal stem cells are a pluripotent population capable of generating multiple stromal cell lineages. MSC, as currently used, are a heterogeneous population of cells isolated by plastic adherence, and propagated by low-density passage. Nonetheless, a recent publication indicates the clonal nature of cell fate outcomes in MSC indicating that a single MSC cell can give rise to two or three mesenchymal lineages one of which is usually bone cells (Pittenger et al., 1999). These studies are consistent with earlier reports that demonstrated the osteogenic potential of bone marrow stromal cells, in particular the so-called CFU-f from both mice and human (Friedenstein et al., 1968; Reddi and Huggins, 1972; Friedenstein et al., 1982; Ashton et al., 1985; Bleiberg, 1985; Gronthos et al., 1994; Gronthos et al., 1999).

Single-cell isolation of human MSC generated clones that express the same surface phenotype as unfractionated MSC (Pittenger et al., 1999). Interestingly, of the 6 MSC clones evaluated, 2 retained osteogenic, chrondrogenic and adipogenic potential; others were bipotent (either osteo-plus chondrogenic potential, or osteo-adipocytic potential) or were uni-lineage (chondrocyte). This suggests that MSC themselves are heterogeneous in nature (although culture conditions also may have led to loss of lineage potential). To date, the self-renewal capacity of MSC remains in question. Nonetheless, these in vitro studies and other in vivo studies (Kadiyala et al., 1997; Petite et al., 2000; Krebsbach et al., 1999) show that MSC can commit to the bone cell lineage and develop to the state of matrix mineralization in vitro, or bone formation in vivo.

Preosteoblasts.

Preosteoblasts are intermediate between osteoprogenitor cells and osteoblasts. They show increasing expression of bone phenotypic markers such as alkaline phosphatase (Kale et al., 2000). They have a more limited proliferative capacity, but nonetheless continue to divide and produce more preosteoblasts or osteoblasts.

Osteoblasts.

An osteoblast is a mononucleate cell that is responsible for bone formation. Osteoblasts produce osteoid, which is composed mainly of Type I collagen. Osteoblasts are also responsible for mineralization of the osteoid matrix. Bone is a dynamic tissue that is constantly being reshaped by osteoblasts, which build bone, and osteoclasts, which resorb bone. Osteoblast cells tend to decrease in number and activity as individuals become elderly, thus decreasing the natural renovation of the bone tissue.

Osteoblasts arise from osteoprogenitor cells located in the periosteum and the bone marrow. Osteoprogenitors are immature progenitor cells that express the master regulatory transcription factor Cbfa1/Runx2. Osteoprogenitors are induced to differentiate under the influence of growth factors, in particular the bone morphogenetic proteins (BMPs). Aside from BMPs, other growth factors including fibroblast growth factor (FGF), platelet-derived growth factor (PDGF), transforming growth factor β (TGF-β) may promote the division of osteoprogenitors and potentially increase osteogenesis. Once osteoprogenitors start to differentiate into osteoblasts, they begin to express a range of genetic markers including Osterix, Col1, ALP, osteocalcin, osteopontin, and osteonectin. Although the term osteoblast implies an immature cell type, osteoblasts are in fact the mature bone cells entirely responsible for generating bone tissue in animals and humans.

Osteoclasts.

An osteoclast is a type of bone cell that removes bone tissue by removing its mineralized matrix. This process is known as bone resorption. Osteoclasts and osteoblasts are instrumental in controlling the amount of bone tissue: osteoblasts form bone, osteoclasts resorb bone. Osteoclasts are formed by the fusion of cells of the monocyte-macrophage cell lineage. Osteoclasts are characterized by high expression of tartrate resistant acid phosphatase (TRAP) and cathepsin K.

Osteoclast formation requires the presence of RANK ligand (receptor activator of nuclear factor κβ) and M-CSF (Macrophage colony-stimulating factor). These membrane bound proteins are produced by neighbouring stromal cells and osteoblasts; thus requiring direct contact between these cells and osteoclast precursors. M-CSF acts through its receptor on the osteoclast, c-fms (colony stimulating factor 1 receptor), a transmembrane tyrosine kinase-receptor, leading to secondary messenger activation of tyrosine kinase Src. Both of these molecules are necessary for osteoclastogenesis and are widely involved in the differentiation of monocyte/macrophage derived cells. RANKL is a member of the tumor necrosis family (TNF), and is essential in osteoclastogenesis. RANKL knockout mice exhibit a phenotype of osteopetrosis and defects of tooth eruption, along with an absence or deficiency of osteoclasts. RANKL activates NF-κβ (nuclear factor-κβ) and NFATc1 (nuclear factor of activated t cells, cytoplasmic, calcineurin-dependent 1) through RANK. NF-κβ activation is stimulated almost immediately after RANKL-RANK interaction occurs, and is not upregulated. NFATc1 stimulation, however, begins ~24-48 hours after binding occurs and its expression has been shown to be RANKL dependent. Osteoclast differentiation is inhibited by osteoprotegerin (OPG), which binds to RANKL thereby preventing interaction with RANK.

B. Bone Formation

The formation of bone during the fetal stage of development occurs by two processes: intramembranous ossification and endochondral ossification.

Intramembranous ossification mainly occurs during formation of the flat bones of the skull; the bone is formed from mesenchyme tissue. The steps in intramembranous ossification are development of ossification center, calcification, formation of trabeculae and development of periosteum.

Endochondral ossification, on the other hand, occurs in long bones, such as limbs; the bone is formed around a cartilage template. The steps in endochondral ossification are development of cartilage model, growth of cartilage model, development of the primary ossification center and development of the secondary ossification center.

Endochondral ossification begins with points in the cartilage called "primary ossification centers." They mostly appear during fetal development, though a few short bones begin their primary ossification after birth. They are responsible for the formation of the diaphyses of long bones, short bones and certain parts of irregular bones. Secondary ossification occurs after birth, and forms the epiphyses of long bones and the extremities of irregular and flat bones. The diaphysis and both epiphyses of a long bone are separated by a growing zone of cartilage (the epiphyseal plate). When the child reaches skeletal maturity (18 to 25 years of age), all of the cartilage is replaced by bone, fusing the diaphysis and both epiphyses together (epiphyseal closure).

Remodeling or bone turnover is the process of resorption followed by replacement of bone with little change in shape and occurs throughout a person's life. Osteoblasts and osteoclasts, coupled together via paracrine cell signalling, are referred to as bone remodeling units. The purpose of remodeling is to regulate calcium homeostasis, repair microdamaged bones (from everyday stress) but also to shape and sculpture the skeleton during growth.

The process of bone resorption by the osteoclasts releases stored calcium into the systemic circulation and is an important process in regulating calcium balance. As bone formation actively fixes circulating calcium in its mineral form, removing it from the bloodstream, resorption actively unfixes it thereby increasing circulating calcium levels. These processes occur in tandem at site-specific locations.

Repeated stress, such as weight-bearing exercise or bone healing, results in the bone thickening at the points of maximum stress (Wolff's law). It has been hypothesized that this is a result of bone's piezoelectric properties, which cause bone to generate small electrical potentials under stress.

III. TREATMENTS

A. Bone Diseases and Conditions

There is a plethora of conditions which are characterized by the need to enhance bone formation or to inhibit bone resorption and thus would benefit from the use of anti-TGF-β antibodies or combinations of anti-TGF-β antibodies and second agents as described above or cells treated therewith in promoting bone formation and/or bone repair. Perhaps the most obvious is the case of bone fractures, where it would be desirable to stimulate bone growth and to hasten and complete bone repair. Agents that enhance bone formation would also be useful in facial reconstruction procedures. Other bone deficit conditions include bone segmental defects, periodontal disease, metastatic bone disease, osteolytic bone disease and conditions where connective tissue repair would be beneficial, such as healing or regeneration of cartilage defects or injury. Also of great significance is the chronic condition of osteoporosis, including age-related osteoporosis and osteoporosis associated with post-menopausal hormone status. Other conditions characterized by the need for bone growth include primary and secondary hyperparathyroidism, disuse osteoporosis, diabetes-related osteoporosis, and glucocorticoid-related osteoporosis. Several other conditions, such as, for example, vitamin D deficiency, exists.

Fracture.

The first example is the otherwise healthy individual who suffers a fracture. Often, clinical bone fracture is treated by casting to alleviate pain and allow natural repair mechanisms to repair the wound. There has been progress in the treatment of fracture in recent times, however, even without considering the various complications that may arise in treating fractured bones, any new procedures to increase bone healing in normal circumstances would represent a great advance.

Periodontal Disease.

Progressive periodontal disease leads to tooth loss through destruction of the tooth's attachment to the surrounding bone. Approximately 5-20% of the U.S. population (15-60 million individuals) suffers from severe generalized periodontal disease, and there are 2 million related surgical procedures. Moreover, if the disease is defined as the identification of at least one site of clinical attachment loss, then approximately 80% of all adults are affected, and 90% of those aged 55 to 64 years. If untreated, approximately 88% of affected individuals show moderate to rapid progression of the disease which shows a strong correlation with age. The major current treatment for periodontal disease is regenerative therapy consisting of replacement of lost periodontal tissues. The lost bone is usually treated with an individual's own bone and bone marrow, due to their high osteogenic potential. Bone allografts (between individuals) can also be performed using stored human bone. Although current periodontal cost analyses are hard to obtain, the size of the affected population and the current use of bone grafts as a first-order therapy strongly suggest that this area represents an attractive target for bone-building therapies.

Osteopenia/Osteoporosis.

The terms osteopenia and osteoporosis refers to a heterogeneous group of disorders characterized by decreased bone mass and fractures. Osteopenia is a bone mass that is one or more standard deviations below the mean bone mass for a population; osteoporosis is defined as 2.5 SD or lower. An estimated 20-25 million people are at increased risk for fracture because of site-specific bone loss. Risk factors for osteoporosis include increasing age, gender (more females), low bone mass, early menopause, race (Caucasians in general; asian and hispanic females), low calcium intake, reduced physical activity, genetic factors, environmental factors (including cigarette smoking and abuse of alcohol or caffeine), and deficiencies in neuromuscular control that create a propensity to fall.

More than a million fractures in the U.S. each year can be attributed to osteoporosis. In economic terms, the costs (exclusive of lost wages) for osteoporosis therapies are $35 billion worldwide. Demographic trends (i.e., the gradually increasing age of the U.S. population) suggest that these costs may increase to $62 billion by the year 2020. Clearly, osteoporosis is a significant health care problem.

Osteoporosis, once thought to be a natural part of aging among women, is no longer considered age or gender-dependent. Osteoporosis is defined as a skeletal disorder characterized by compromised bone strength predisposing to an increased risk of fracture. Bone strength reflects the integration of two main features: bone density and bone quality. Bone density is expressed as grams of mineral per area or volume and in any given individual is determined by peak bone mass and amount of bone loss. Bone quality refers to architecture, turnover, damage accumulation (e.g., microfractures) and mineralization. A fracture occurs when a failure-inducing force (e.g., trauma) is applied to osteoporotic bone.

Current therapies for osteoporosis patients focus on fracture prevention, not for promoting bone formation or fracture repair. This remains an important consideration because of the literature, which clearly states that significant morbidity and mortality are associated with prolonged bed rest in the elderly, particularly those who have suffered hip fractures. Complications of bed rest include blood clots and pneumonia. These complications are recognized and measures are usually taken to avoid them, but these is hardly the best approach to therapy. Thus, the osteoporotic patient population would benefit from new therapies designed to strengthen bone and speed up the fracture repair process, thus getting these people on their feet before the complications arise.

Bone Reconstruction/Grafting.

A fourth example is related to bone reconstruction and, specifically, the ability to reconstruct defects in bone tissue that result from traumatic injury; as a consequence of cancer or cancer surgery; as a result of a birth defect; or as a result of aging. There is a significant need for more frequent orthopedic implants, and cranial and facial bone are particular targets for this type of reconstructive need. The availability of new implant materials, e.g., titanium, has permitted the repair of relatively large defects. Titanium implants provide excellent temporary stability across bony defects and are an excellent material for bone implants or artificial joints such as hip, knee and joint replacements. However, experience has shown that a lack of viable bone binding to implants the defect can result in exposure of the appliance to infection, structural instability and, ultimately, failure to repair the defect. Thus, a therapeutic agent that stimulates bone formation on or around the implant will facilitate more rapid recovery.

Autologous bone grafts are another possibility, but they have several demonstrated disadvantages in that they must be harvested from a donor site such as iliac crest or rib, they usually provide insufficient bone to completely fill the defect, and the bone that does form is sometimes prone to infection and resorption. Partially purified xenogeneic preparations are not practical for clinical use because microgram quantities are purified from kilograms of bovine bone, making large scale commercial production both costly and impractical. Allografts and demineralized bone preparations are therefore often employed, but suffer from their devitalized nature in that they only function as scaffolds for endogenous bone cell growth.

Microsurgical transfers of free bone grafts with attached soft tissue and blood vessels can close bony defects with an immediate source of blood supply to the graft. However, these techniques are time consuming, have been shown to produce a great deal of morbidity, and can only be used by specially trained individuals. Furthermore, the bone implant is often limited in quantity and is not readily contoured. In the mandible, for example, the majority of patients cannot wear dental appliances using presently accepted techniques (even after continuity is established), and thus gain little improvement in the ability to masticate.

In connection with bone reconstruction, specific problem areas for improvement are those concerned with treating large defects, such as created by trauma, birth defects, or particularly, following tumor resection; and also the area of artificial joints. The success of orthopaedic implants, interfaces and artificial joints could conceivably be improved if the surface of the implant, or a functional part of an implant, were to be coated with a bone stimulatory agent. The surface of implants could be coated with one or more appropriate materials in order to promote a more effective interaction with the biological site surrounding the implant and, ideally, to promote tissue repair.

Primary Bone Cancer and Metastatic Bone Disease.

Bone cancer occurs infrequently while bone metastases are present in a wide range of cancers, including thyroid, kidney, and lung. Metastatic bone cancer is a chronic condition; survival from the time of diagnosis is variable depending on tumor type. In prostate and breast cancer and in multiple myeloma, survival time is measurable in years. For advanced lung cancer, it is measured in months. Cancer symptoms include pain, hypercalcemia, pathologic fracture, and spinal cord or nerve compression. Prognosis of metastatic bone cancer is influenced by primary tumor site, presence of extra-osseous disease, and the extent and tempo of the bone disease. Bone cancer/metastasis progression is determined by imaging tests and measurement of bone specific markers. Recent investigations show a strong correlation between the rate of bone resorption and clinical outcome, both in terms of disease progression or death.

Multiple Myeloma.

Multiple myeloma (MM) is a B-lymphocyte malignancy characterized by the accumulation of malignant clonal plasma cells in the bone marrow. The clinical manifestations of the disease are due to the replacement of normal bone marrow components by abnormal plasma cells, with subsequent overproduction of a monoclonal immunoglobulin (M protein or M component), bone destruction, bone pain, anemia, hypercalcemia and renal dysfunction.

As distinct from other cancers that spread to the bone (e.g., breast, lung, thyroid, kidney, prostate), myeloma bone disease (MBD) is not a metastatic disease. Rather, myeloma cells are derived from the B-cells of the immune system that normally reside in the bone marrow and are therefore intimately associated with bone. Indeed, the bone marrow microenvironment plays an important role in the growth, survival and resistance to chemotherapy of the myeloma cells, which, in turn, regulate the increased bone loss associated with this disorder (world-wide-web at multiplemyeloma.org). Over 90% of myeloma patients have bone involvement, versus 40-60% of cancer patients who have bone metastasis, and over 80% have intractable bone pain. Additionally, approximately 30% of myeloma patients have hypercalcemia that is a result of the increased osteolytic activity associated with this disease (Cavo et al., 2006).

Common problems in myeloma are weakness, confusion and fatigue due to hypercalcemia. Headache, visual changes and retinopathy may be the result of hyperviscosity of the blood depending on the properties of the paraprotein. Finally, there may be radicular pain, loss of bowel or bladder control (due to involvement of spinal cord leading to cord compression) or carpal tunnel syndrome and other neuropathies (due to infiltration of peripheral nerves by amyloid). It may give rise to paraplegia in late presenting cases.

Myeloma Bone Disease.

As discussed above, unlike the osteolysis associated with other bone tumors, the MBD lesions are unique in that they do not heal or repair, despite the patients' having many years of complete remission. Mechanistically, this seems to be related to the inhibition and/or loss of the bone-forming osteoblast during disease progression. Indeed, bone marker studies and histomorphometry indicate that both the bone-resorbing osteoclast and osteoblast activity are increased, but balanced early in the disease, whereas overt MBD shows high osteoclast activity and low osteoblast activity. Thus, MBD is a disorder in which bone formation and bone loss are uncoupled and would benefit from therapies that both stimulate bone formation and retard its loss.

A number of therapeutic approaches have been used in MBD, with the endpoints of treating pain, hypercalcemia, or the reduction of skeletal related events (SRE). Many of these may present serious complications. Surgery, such as vertebroplasty or kyphoplasty, that is performed for stability and pain relief has the attendant surgical risks (e.g., infection) made worse by a compromised immune system and does not reverse existing skeletal defects. Radiation therapy and radioisotope therapy are both used to prevent/control disease progression and have the typical risks of irradiation therapies. More recently, drugs such as the bisphosphonates that inhibit osteoclast activity have become a standard of therapy for MBD, despite the fact that they work poorly in this disorder. In 9 major double-blind, placebo-controlled trials on bisphosphonates, only 66% of patients showed an effective reduction in pain; 56% showed a reduction in SRE and only 1 of the 9 demonstrated a survival benefit.

B. Combination Treatments

As discussed, the present invention provides for the treatment of bones disease and bone trauma by stimulating the production of new bone tissue. Other agents may be used in combination with the anti-TGF-β antibodies of the present invention. More generally, these agents would be provided in a combined amount (along with the anti-TGF-β antibodies) to produce any of the effects discussed above. This process may involve contacting the cell or subject with both agents at the same time. This may be achieved by contacting the cell with a single composition or pharmacological formulation that includes both agents, or by contacting the cell or subject with two distinct compositions or formulations, at the same time, wherein one composition includes the intracellular inhibitor and the other includes the second agent.

Alternatively, one agent may precede or follow the other by intervals ranging from minutes to weeks. In embodiments where the agents are applied separately to the cell or subject, one would generally ensure that a significant period of time did not expire between the time of each delivery, such that the agents would still be able to exert an advantageously combined effect on the cell or subject. In such instances, it is contemplated that one may contact the cell or subject with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Various combinations may be employed, the anti-TGF-β antibody is "A" and the other agent is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration protocols and formulation of such agents will generally follow those of standard pharmaceutical drugs, as discussed further below. Combination agents include bisphosphonates (Didronel™, Fosamax™ and Actonel™), SERMs (Evista) or other hormone derivatives, and Parathyroid Hormone (PTH) analogs.

IV. PHARMACEUTICAL FORMULATIONS AND DELIVERY

A. Compositions and Routes

Pharmaceutical compositions of the present invention comprise an effective amount of one or more anti-TGF-β antibodies dissolved or dispersed in a pharmaceutically acceptable carrier. The phrases "pharmaceutical or pharmacologically acceptable" refer to molecular entities and compositions that do not produce an adverse, allergic or other untoward reaction when administered to an animal, such as, for example, a human, as appropriate. The preparation of a pharmaceutical composition that contains at least one anti-TGF-β antibody, and optionally an additional active ingredient, will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, 1289-1329, incorporated herein by reference). Except insofar as any conventional carrier is incompatible with the active ingredient, its use in the pharmaceutical compositions is contemplated.

The anti-TGF-β antibody may be admixed with different types of carriers depending on whether it is to be administered orally or by injection. The present invention can be administered buccally, intravenously, intradermally, transdermally, intrathecally, intraarterially, intraperitoneally, intranasally, intravaginally, intrarectally, topically, intramuscularly, intratumorally, into tumor vasculature, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., nanoparticles, liposomes), or by other method or any combination of the forgoing as would be known to one of ordinary skill in the art (see, for example, Remington's Pharmaceutical Sciences, 18th Ed. Mack Printing Company, 1990, incorporated herein by reference). In particular, the anti-TGF-β antibody is formulated into a syringeable composition for use in intravenous administration.

The anti-TGF-β antibody may be formulated into a composition in a free base, neutral or salt form or ester. It may also be synthesized/formulated in a prodrug form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric, fumaric, or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include anti-TGF-β antibodies, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally-occurring or synthetic (i.e., designed or produced by man). Lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof.

One of ordinary skill in the art would be familiar with the range of techniques that can be employed for dispersing a composition in a lipid vehicle. For example, the anti-TGF-β antibodies may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, anti-TGF-β antibody pharmaceutical compositions may comprise, for example, at least about 0.1% of the antagonist, about 0.5% of the antagonist, or about 1.0% of the antagonist. In other embodiments, the antagonist may comprise between about 2% to about 75% of the weight of the unit, or between about 25% to about 60%, for example, and any range derivable therein. Naturally, the amount of the antagonist in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose of anti-TGF-β antibodies may also comprise from about 0.1 microgram/kg/body weight, about 0.2 microgram/kg/body weight, about 0.5 microgram/kg/body weight, about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In particular embodiments of the present invention, the anti-TGF-β antibodies are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tablets, troches, capsules, elixirs, suspensions, syrups, wafers, and the like (Mathiowitz et al., 1997; Hwang et al., 1998; U.S. Pat. Nos. 5,641,515, 5,580, 579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration, such as in the treatment of periodontal disease, the compositions of the present invention may alternatively be incorporated with one or more excipients in the form of a mouthwash, dentifrice, buccal tablet, oral spray, gel or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet, gel or solution form that may be placed under the tongue, along the gum line, brushed on to teeth surfaces, or otherwise dissolved in the mouth. U.S. Pat. Nos. 6,074,674 and 6,270,750, both incorporated by reference, describe topical, sustained release compositions for periodontal procedures.

In further embodiments, anti-TGF-β antibodies may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,537,514, 6,613,308, 5,466,468, 5,543,158; 5,641, 515; and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it may be desirable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sustained release formulations for treating of bone conditions include U.S. Pat. Nos. 4,722,948, 4,843,112, 4,975,526, 5,085,861, 5,162,114, 5,741,796 and 6,936,270, all of which are incorporated by reference. Methods and injectable compositions for bone repair are described in U.S. Pat. Nos. 4,863,732, 5,531,791, 5,840,290, 6,281,195, 6,288,043, 6,485,754, 6,662,805 and 7,008,433, all of which are incorporated by reference.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

B. Devices

In addition to providing anti-TGF-β antibodies for administration by routes discussed above, such agents, alone or in combination, may be used in the context of devices, such as implants. A variety of bone related implants are contemplated, including dental implants, joint implants such as hips, knees, and elbows, vertebral/spinal implants, and others. The anti-TGF-β antibodies may be impregnated in a surface of the implant, including in a bioactive matrix or coating. The inhibitor may be further formulated to sustained, delayed, prolonged or time release. The coating may comprise polymers, for example, such as those listed below. The following is a list of U.S. patents relating to bone implants and devices which may be utilized in accordance with this embodiment of the invention:

TABLE 1

BONE IMPLANT PATENTS

| U.S. Patent* | Patent Title |
| --- | --- |
| 7,044,972 | Bone implant, in particular, an inter-vertebral implant |
| 7,022,137 | Bone hemi-lumbar interbody spinal fusion implant having an asymmetrical leading end and method of installation thereof |
| 7,001,551 | Method of forming a composite bone material implant |
| 6,994,726 | Dual function prosthetic bone implant and method for preparing the same |
| 6,989,031 | Hemi-interbody spinal implant manufactured from a major long bone ring or a bone composite |
| 6,988,015 | Bone implant |
| 6,981,975 | Method for inserting a spinal fusion implant having deployable bone engaging projections |
| 6,981,872 | Bone implant method of implanting, and kit for use in making implants, particularly useful with respect to dental implants |
| 6,929,662 | End member for a bone fusion implant |
| 6,923,830 | Spinal fusion implant having deployable bone engaging projections |
| 6,921,264 | Implant to be implanted in bone tissue or in bone tissue supplemented with bone substitute material |
| 6,918,766 | Method, arrangement and use of an implant for ensuring delivery of bioactive substance to the bone and/or tissue surrounding the implant |
| 6,913,621 | Flexible implant using partially demineralized bone |
| 6,899,734 | Modular implant for fusing adjacent bone structure |
| 6,860,884 | Implant for bone connector |
| 6,852,129 | Adjustable bone fusion implant and method |
| 6,802,845 | Implant for bone connector |
| 6,786,908 | Bone fracture support implant with non-metal spacers |
| 6,767,367 | Spinal fusion implant having deployable bone engaging projections |
| 6,761,738 | Reinforced molded implant formed of cortical bone |
| 6,755,832 | Bone plate implant |
| 6,730,129 | Implant for application in bone, method for producing such an implant, and use of such an implant |
| 6,689,167 | Method of using spinal fusion device, bone joining implant, and vertebral fusion implant |
| 6,689,136 | Implant for fixing two bone fragments to each other |
| 6,666,890 | Bone hemi-lumbar interbody spinal implant having an asymmetrical leading end and method of installation thereof |
| 6,652,592 | Segmentally demineralized bone implant |
| 6,648,917 | Adjustable bone fusion implant and method |
| 6,607,557 | Artificial bone graft implant |
| 6,599,322 | Method for producing undercut micro recesses in a surface, a surgical implant made thereby, and method for fixing an implant to bone |

TABLE 1-continued

BONE IMPLANT PATENTS

| U.S. Patent* | Patent Title |
| --- | --- |
| 6,562,074 | Adjustable bone fusion implant and method |
| 6,562,073 | Spinal bone implant |
| D473,944 | Bone implant |
| 6,540,770 | Reversible fixation device for securing an implant in bone |
| 6,537,277 | Implant for fixing a bone plate |
| 6,506,051 | Bone implant with intermediate member and expanding assembly |
| 6,478,825 | Implant, method of making same and use of the implant for the treatment of bone defects |
| 6,458,136 | Orthopaedic instrument for sizing implant sites and for pressurizing bone cement and a method for using the same |
| 6,447,545 | Self-aligning bone implant |
| 6,436,146 | Implant for treating ailments of a joint or a bone |
| 6,371,986 | Spinal fusion device, bone joining implant, and vertebral fusion implant |
| 6,370,418 | Device and method for measuring the position of a bone implant |
| 6,364,880 | Spinal implant with bone screws |
| 6,350,283 | Bone hemi-lumbar interbody spinal implant having an asymmetrical leading end and method of installation thereof |
| 6,350,126 | Bone implant |
| 6,287,343 | Threaded spinal implant with bone ingrowth openings |
| 6,270,346 | Dental implant for bone regrowth |
| 6,248,109 | Implant for interconnecting two bone fragments |
| 6,217,617 | Bone implant and method of securing |
| 6,214,050 | Expandable implant for inter-bone stabilization and adapted to extrude osteogenic material, and a method of stabilizing bones while extruding osteogenic material |
| 6,213,775 | Method of fastening an implant to a bone and an implant therefor |
| 6,206,923 | Flexible implant using partially demineralized bone |
| 6,203,545 | Implant for fixing bone fragments after an osteotomy |
| 6,149,689 | Implant as bone replacement |
| 6,149,688 | Artificial bone graft implant |
| 6,149,686 | Threaded spinal implant with bone ingrowth openings |
| 6,126,662 | Bone implant |
| 6,083,264 | Implant material for replacing or augmenting living bone tissue involving thermoplastic syntactic foam |
| 6,058,590 | Apparatus and methods for embedding a biocompatible material in a polymer bone implant |
| 6,018,094 | Implant and insert assembly for bone and uses thereof |
| 5,976,147 | Modular instrumentation for bone preparation and implant trial reduction of orthopedic implants |
| 5,906,488 | Releasable holding device preventing undesirable rotation during tightening of a screw connection in a bone anchored implant |
| 5,899,939 | Bone-derived implant for load-supporting applications |
| 5,895,425 | Bone implant |
| 5,890,902 | Implant bone locking mechanism and artificial periodontal ligament system |
| 5,885,287 | Self-tapping interbody bone implant |
| 5,819,748 | Implant for use in bone surgery |
| 5,810,589 | Dental implant abutment combination that reduces crestal bone stress |
| 5,759,035 | Bone fusion dental implant with hybrid anchor |
| 5,720,750 | Device for the preparation of a tubular bone for the insertion of an implant shaft |
| 5,709,683 | Interbody bone implant having conjoining stabilization features for bony fusion |
| 5,709,547 | Dental implant for anchorage in cortical bone |
| 5,674,725 | Implant materials having a phosphatase and an organophosphorus compound for in vivo mineralization of bone |
| 5,658,338 | Prosthetic modular bone fixation mantle and implant system |
| D381,080 | Combined metallic skull base surgical implant and bone flap fixation plate |
| 5,639,402 | Method for fabricating artificial bone implant green parts |
| 5,624,462 | Bone implant and method of securing |
| D378,314 | Bone spinal implant |
| 5,607,430 | Bone stabilization implant having a bone plate portion with integral cable clamping means |
| 5,571,185 | Process for the production of a bone implant and a bone implant produced thereby |
| 5,456,723 | Metallic implant anchorable to bone tissue for replacing a broken or diseased bone |
| 5,441,538 | Bone implant and method of securing |
| 5,405,388 | Bone biopsy implant |
| 5,397,358 | Bone implant |
| 5,383,935 | Prosthetic implant with self-generated current for early fixation in skeletal bone |
| 5,364,268 | Method for installing a dental implant fixture in cortical bone |
| 5,312,256 | Dental implant for vertical penetration, adapted to different degrees of hardness of the bone |

*The preceding patents are all hereby incorporated by reference in their entirety.

V. SCREENING ASSAYS

In still further embodiments, the present invention provides methods identifying new and useful antibodies against TGF-β for use in stimulating bone production. For example, a method generally comprises:

(a) providing a candidate antibody;

(b) admixing the candidate modulator with a cell or a suitable experimental animal;

(c) measuring osteoblast or osteoclast activity, or bone growth, strength, mass or formation; and (d) comparing the characteristic measured in step (c) with that observed in the absence of the candidate, wherein a difference between the measured characteristic indicates that said candidate is, indeed, a bone production stimulator.

Assays may be conducted in isolated cells or in organisms including transgenic animals. Bone formation can be identified by the von Kossa or Alzarin Red stains, FTIR or Raman spectrometric analysis, or by fluorochromes linked to compounds that bind bone.

It will, of course, be understood that all the screening methods of the present invention are useful in themselves notwithstanding the fact that effective candidates may not be found. The invention provides methods for screening for such candidates, not solely methods of finding them.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods

Antibodies.

The 1D11 antibody was generated by Genzyme Corporation (Framingham). Control antibody (13C4) consistent of an identical IgG complex lacking any TGF-β binding capabilities.

Treatment Regimen.

Normal 13-week old male C57Bl/6 mice (Harlan) (n=5) were treated with 10 mg/kg/×3 week of 1D11 or control antibody. Each reagent was administered by sterile intraperitoneal injection over a 4 week time period (FIG. 1). All animal procedures were conducted in accordance with IACUC protocols approved by Vanderbilt University Medical Center.

Imaging.

Tibia and femure were analyzed by μCT scanning (μCT40, Scanco) at an isotropic voxel size of 12 μm (55Kv). After the growth plate was identified in each scan set, the metaphyseal region 200 μm below this area was scanned and analyzed for alterations in trabecular bone parameters (Threshold 280).

Histology and Histomorphometry.

Lumbar vertebral bodies (L3-5) and long bones were collected following sacrifice and fixed for up to 48 hrs in 10% formalin. Undecalcified regions of vertebrae were processed and embedded in a methylmethacrylate-based resin and sectioned at 5 μm. Sections were deplasticized and stained for bound calcium ions using the Von Kossa procedure with a van Gieson counterstain, or using a post-coupling staining technique for tartrate-resistant acid phosphatase (TRAP). Long bones were decalcified for 2 weeks in 10% EDTA and processed to paraffin wax. Samples were sectioned at 5 μm and stated with H&E/Orange G, or for TRAP activity. Bone volume, cellular distribution was quantified histomorphometrically using Osteomeasure quantification software (Osteometrics).

Gene Expression.

The RANKL/OPG gene expression ratio was assessed in 1D11- or control-treated T23 osteoblast cells, with RNA isolated using RNEasy extraction kits (Qiagen). Validated Taqman primers were purchases and samples analyzed using a 7300 Real Time PCR system (Applied Biosystems) under conditions recommended by the manufacturer. Osteogeneic expression was assessed using standard RT-PCR techniques.

Protein Expression.

Normal serum was isolated from treated and untreated mice by exsanguination prior to sacrifice. Serum was assessed by enzyme linked immunosorbent assay (ELISA) for levels of soluble RANKL or OPG protein using the Quantikine Immunoassay system (R&D Systems) with concentrate and ×5 serum dilution used for RANKL and OPG, respectively.

Urine Resporption Assay.

Urine samples were collected from all animals prior to sacrifice. The collagen breakdown product deoxypyridinoline (DPD) was quantified by ELISA using the MicroVue-DPD assay (Quidel Corp.) following manufacturer's guidelines and normalized to urinary creatinine levels (MicroVue-Creatinine, Quidel Corp.).

Biochemical Testing.

The strength and modulus of the diaphyseal region of the femur were analyzed biochemically. Fresh femurs were horizontally positioned on support rollers and monotonically loaded on three-point bending at a rate of 3 mm/min, using a material testing system (Dynamight 8841; Instron). The force displacement curve was recorded to provide the maximum force endured by the bone an the initial stiffness. Using uCT-derived moment of inertia and flexural equations from beam theory (Schriefer et al., 2005), the inventors converted these structural properties to whole bone bending strength and modulus.

Raman Microspectroscopy.

The chemical composition of the bone tissue was characterized by confocal Raman microspectroscopy (Renishaw). Tibia were embedded in PMMA and cut at the metaphysis below the growth place to expose a cross-section of the cortex. This surface was ground on successive grits of silicon carbide paper and polished with 1 μm alumina slurry. A 50× objective focuses the laser (785 nm laser diode source) to a 3 μm region below the surface of the tissue, and inelastic light was collected by a Renishaw spectrograph (1 $cm^{-1}$ spectral resolution). The measured spectra consisted of three accumulations with an integration time of 10 s each. Using custom Matlab scripts, background fluorescence in the spectra was subtraced by a modified polynomial fitting algorithm (Lieber et al., 2003). Spectra were collected from 10 trabecular locations with the tibial metaphysis (ground below the growth plate). Mineral-to-collagen ratio was calculated as the v1 phosphate peak intensity (962 $cm^{-1}$) per proline peak intensity (856 $cm^{-1}$) and averaged per bone.

Nanoindentation.

Modulus at the tissue level was quantified by nanoindentation. Resin-embedded regions of the tibial diaphysis were probed using a Nanoidenter XP (MTS XP). A Berkovitch diamond tip (inclination angle: 142.3°; radius: 100 nm) was pressed into the surface using trapezoidal loading scheme as follows: 1) load at a strain rate of 0.5/s to a depth of 1 μm, 2) hold at $P_{max}$ for 10 seconds, 3) unload at 350 μN $s^{-1}$ to 90% of $P_{max}$, and 4) leave the indenter on the surface for 60 seconds in order to establish the thermal drift. From the resulting force-displacement curve, the elastic modulus (E) of the tissue at the point of indenting (0.25 μm resolution) was calculated following the methods of Oliver and Pharr (2004). This involves an initial calibration procedure using fused silica to establish the relationship between depth of indent and contact area of the tip, and to determine the slope of the unloading portion of the force-displacement curve. Ten indents were collected per bone, with data represented as mean±SE.

Statistical Analysis.

Statistically significant values were determined by the Mann-Whitney and Students t-test with p-values less than 0.05 considered significant.

Example 2

Results

Figure 3B:
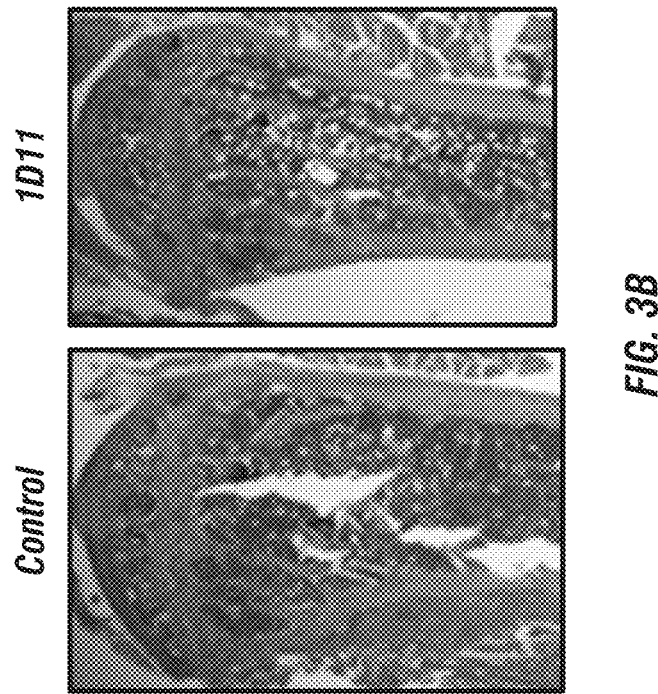
FIGS. 3A-B—Histomorphometric analysis. Tissue sections of undecalcified lumbar vertebrate from animals treated with 1D11 showed a significant increase in BV/TV and positive changes in trabecular parameters, compared to control animals (FIG. 3A, Von Kossa/Van Gieson, *=p<0.05). Long bone volume was also dramatically increased (FIG. 3B, H&E).
Figure 3A:
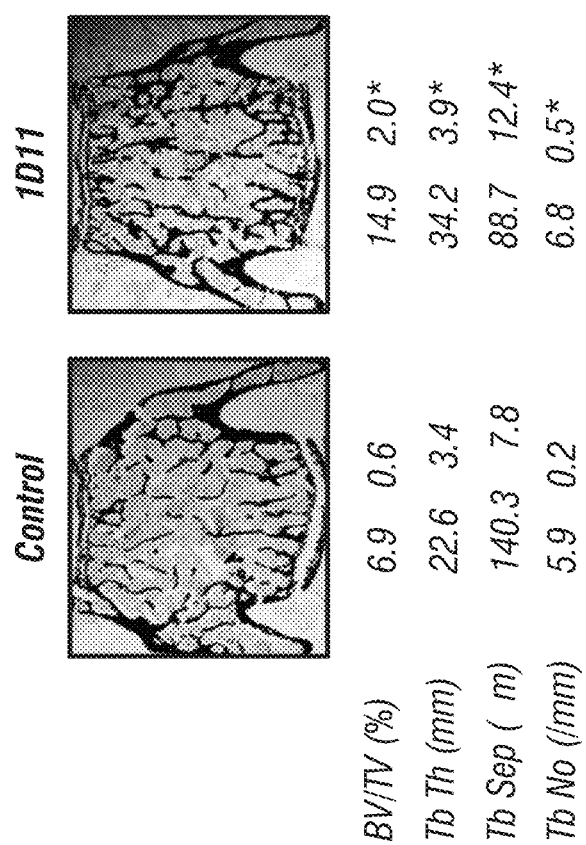

Inhibition of TGF-β by 1D11 antibody treatment, outlined in FIG. 1, significantly increased long bone volume compared to controls (FIGS. 2A-B). Trabecular bone at the tibial metaphysis analyzed by μCT scanning showed a dramatic increase in overall BV/TV (FIG. 2C), bone mineral density (BMD) (FIG. 2D), trabecular thickness (FIG. 2F) and decreased trabecular separation (FIG. 2F) in animals treated with 1D11 compared to control-treated mice. Histomorphometric analysis of undecalcified sections from lumbar vertebra supported μCT analysis of long bones. 1D11-mediated TGF-β inhibition led to a 54% increase in trabecular BV/TV. This increase in bone was accompanied by greater trabecular number, decreased trabecular separation and increased trabecular thickness (FIGS. 3A-B).

An analysis of bone cell distribution in TRAP-stained vertebral sections showed significantly reduced osteoclast numbers and surface area following 1D11 treatment (FIGS. 4A-C). In contrast, elevated osteoblast numbers and osteoblast area lining the bone surface in mice receiving 1D11 was observed, compared to controls (FIG. 4D). In addition to alterations in bone cell numbers, overall bone mass and skeletal integrity can also be affected by changes in the remodelling rate of bone. To determine bone turnover rates following treatment with 1D11, the inventors assessed the collagen breakdown product deoxypyridinoline (DPD) in urine samples collected at sacrifice. In support of histomorphometric data, the DPD/creatinine ratio indicated a decrease in resportive activity following treatment with 1D11 (control=39.3±5.6; 1D11=12.0±6.2 µg protein).

It has become very clear over recent years that in addition to the overall quantity of bone present within the skeleton, the quality of bone is also an essential element to be considered when analyzing new therapeutics and their effects on the skeleton. To address this, the inventors performed 3-point bending on excised femurs to determine the effect of 1D11 treatment on the biomechanical properties of bone. Blocking TGF-β signaling resulted in considerably stronger bones with increased whole bone bending strength and modulus (FIG. 5). The effect of 1D11 on skeletal modulus was also examined at a tissue level using nanoindentation. These findings support biomechanical data showing enhanced tissue-level modulus following treatment with 1D11 (Table 2). In addition, Rama microspectroscopy allowed the inventors to analyze and quantify the effect of TGF-β blockade on the compositional components of bone. These studies demonstrated an 11% increase in mineral-to-collagent ratio of trabecular bone in the tibial methaphysis following treatment with 1D11. However, the quality of hydroxyapatite and overall crystallinity of the inorganic component remained unchanged (Table 2).

Skeletal integrity is maintained when osteoblast and osteoclast formation an activity are balanced. A primary mechanism mediating osteoclastic bone resporption occurs via RANKL/OPG expression osteoclasts. As TGF-β has previously been shown to alter the RANKL/OPG ratio) (Mohammad et al., 2009; Karst et al., 2004; Quinn et al., 2001; Thirunavukkarasu et al., 2001), the inventors examined the effect of treatment with 1D11 on RANKL/OPG gene expression in osteobalst cell lines in vitro and assessed RANKL and OPG protein levels in vivo, in serum samples from 1D11- or control-treated animals. In culture, TGF-β treatment decreased RANKL mRNA expression (rankl/gapdh; 1.6±0.2 versus 0.7±0.1) and increased OPG gene expression (opg/gapdh: 1.7±0.1 versus 2.4±0.2). This effect was blocked by the addition of 1D11 to osteobalst cultures. However, no significant changed in individual RANKL (control=31.9±7.6; 1D11=17.0±1.8 pg/ml) or OPG (control=487.7±22.6; 1D11=451.5±20.4 pg/ml) protein levels were detectable in serum samples from treated or untreated mice, although the reduced RANKL levels did lead to a 50% decrease in the overall RANKL/OPG ratio. In addition, the direct effect of TGF-β on osteogenic gene expression was analysis in vitro. Treatment of 2T3 osteoblast cells with TGF-β induced a 49.3% decrease in alkaline phosphatase gene expression and a 331.8% increase in PTHrP expression, as determined by PCR. This increase was completely prevented by treatment with 1D11 in addition to TGF-β. No alterations were observed in the expression levels of runx2, β-catenin, type 1 collagent or osteocalcin, with identical results observed in the MC3T3 osteoblast cell line. Together, these investigations confirm an overall beneficial effect on the skeleton following the neutralization of TGF-β in the bone marrow environment.

TABLE 2

Compositional parameters of treated bone

| | Control | 1D11 |
|---|---|---|
| Nanoindentation | | |
| Tissue-level modulus (GPa) | 22.7 ± 0.5 | 24.3 ± 1.3* |
| Raman microspectroscopy | | |
| Mineral/collagen ratio (%) | 5.5 ± 0.1 | 6.1 ± 0.1* |
| Carbonate substitutions | 0.185 ± 0.012 | 0.169 ± 0.009 |
| Crystallinity | 0.078 ± 0.005 | 0.081 ± 0.002 |

Example 3

Discussion

This study investigates the use of a TGF-β neutralizing antibody as an anabolic bone agent and highlights the potential of TGF-β inhibition as a mechanism to increase bone mass. The inventors employed standard, accepted techniques along with emerging technologies to thoroughly analyze bone volume, density, strength and composition. Together, these studies demonstrate that drugs aimed at blocking the TGF-β signaling pathway have the capacity to positively regulate osteoblast numbers while simultaneously decreasing the amount of active osteoclasts in the marrow. This results in a profound increase in bone volume and quality, similar to that seen in PTH-treated rodent studies (Dempster et al., 1993).

There is a considerable need for more efficacious bone anabolic agents. Currently, the major therapeutic approach to excessive bone loss is through the use of anti-resorptives such as bisphosphonates. While these agents are certainly capable of repressing further bone resorption, they are unable to stimulate new cycles of formation to replace the bone which has been lost. The inventors have shown that targeting TGF-β with a neutralizing antibody has the ability to prevent bone destruction by decreasing osteoclasts, while simultaneously increasing osteoblasts. The direct result is a net improvement in bone mass within the appendicular and axial skeletal regions. Long bones were also shown to be considerably stronger with enhanced matrix compositional properties favorable to normal skeletal function.

Elevated bone loss, such as that seen in osteoporosis, frequently leads to an increase in fracture risk. This feature ultimately results from an overall loss of strength and decreased bone quality within the skeleton. It has been suggested that this deficit in bone quality cannot be accounted for by the decrease in bone volume alone, suggesting an intrinsic defect in the production of new bone matrix in these individuals. Normal bone typically comprises of a balanced ratio of organic collagen matrix and inorganic mineral component. While excessive dysregulation of each element results in profound skeletal defects, the ratio can be modified throughout life to improve the overall strength of bone and resistance to fracture. Treatment with 1D11 increased the mineral to collagen ratio of trabecular bone without impairing the purity of the hydroxyapatite, as assessed by the level of carbonate substitutions within the crystal, suggesting that TGF-β inhibition within this environment favors the production of improved quality bone. Also, the enhanced compositional features of 1D11-treated bone, translate well to an overall increase in bone strength in these animals. This data is supported by genetically modified mouse models where disrupted TGF-β signaling increases bone strength (Balooch et al., 2005), though it was not known whether this system would represent a viable and effective therapeutic approach to improve bone mass. The dramatic beneficial effects reported in our study provide strong evidence for the development of pharmaceutical agents specifically targeted at TGF-β inhibition to enhance bone mass and strength.

Intermittent doses of parathyroid hormone (PTH) currently represent the only clinically available approach to increase bone volume. However, the mechanism through which PTH induces this effect is still not clear. Moreover, continuous PTH treatment is proven to stimulate osteoclastic bone resorption and decrease overall bone mass (Raisz, 2005). Like PTH, neutralizing TGF-β with 1D11 antibody therapy vastly improved skeletal parameters, and like PTH the true mechanism through which this may be occurring is still unknown. But in contrast to the effects of PTH, 1D11 negatively regulates osteoclasts, inhibiting bone degradation and offering a dual approach to enhance bone mass through increased osteoblast numbers and decreased osteoclastic resorption.

Despite a wealth of literature describing TGF-β effects on bone cells, it remains unclear how TGF-β inhibition mediates skeletal events in vivo. Recent studies suggest a dysregulation in primary osteoclastogenic molecules (RANKL/OPG) or ephrin mediated bone remodeling (Mohammad et al., 2009).

The inventors examined soluble RANKL and OPG protein levels in mouse sera following treatment with 1D11 or control and noted a trend toward a decrease in the RANKL/OPG ratio, brought about by decreased RANKL levels. This finding may be associated with the decreased expression of PTHrP observed in osteoblasts treated with 1D11, as PTHrP is known to stimulate RANKL in this cell type (Lee and Lorenzo, 1999; Itoh et al., 2000). While these in vivo observations are consistent with current studies (Mohammad et al., 2009) and suggest that 1D11 treatment could increase bone volume by suppressing TGF-β regulation of RANKL or OPG in osteoblasts, contrasting in vitro molecular studies, indicate that TGF-β treatment leads to a significant reduction in RANKL and increase in OPG mRNA expression, which could be blocked by 1D11. These findings are consistent with published studies documenting TGF-β regulation of RANKL/OPG in vitro (Quinn et al., 2001; Thirunavukkarasu et al., 2001) and strongly suggest a diverse role of TGF-β in normal physiology, which is not well-recapitulated in culture systems, and is likely dependent on the interactions with other regulatory molecules. A careful interpretation of results is therefore necessary when analyzing differences between TGF-β function in vitro and in vivo.

Osteoblasts derive from a mesenchymal stem cell population within the bone marrow. Precursor cells are triggered to commit to the osteoblast lineage by stimulatory factors such as BMP-2 (Katagiri et al., 1990; Takuwa et al., 1991). Molecular analysis of osteogenic gene expression, suggested that osteoblast activity may be altered by 1D11-treatment in vitro, evidenced by increased alkaline phosphatase levels. This finding correlates with published data (Filvaroff et al., 1999; Alliston et al., 2001; Kang et al., 2005), though fails to illustrate any major effect on the maturation of precursors to increase osteoblast numbers, as demonstrated by our in vivo findings. This suggests that local TGF-β inhibition in the bone marrow may influence bone formation during this treatment period, but the true mechanism governing any change in osteoblastogenesis remains unknown.

In addition to direct effects on bone cells, the inventors are unable to exclude a systemic effect of TGF-β in this system. It is plausible that TGF-β control of normal physiological processes negatively impact bone mass, and blocking these effects are ultimately beneficial for skeletal health. It is also possible that TGF-β control of bone cell formation or activity varies temporally as the cellular population of the marrow changes. This would be consistent with in vitro studies describing differential effects on precursor cells compared to mature matrix forming osteoblasts (Mundy and Bonewald, 1990). The inventors used mature C57BI/6 male mice to highlight the beneficial effects of TGF-β blockade on the skeleton. Further studies using bone-loss models will be necessary to assess whether 1D11 treatment improves bone under these conditions. Despite this, our use of C57BI/6 mice, which are reported to have the lowest BMD of all available mouse strains (Beamer et al., 1996), suggests that TGF-β inhibition is likely to improve skeletal properties in low bone mass, aged or osteopenic models also.

In support of this data, small molecules aimed at blocking TGF-β signaling by inhibiting TGF-β receptor kinase activity have recently been shown to increase bone mass (Mohammad et al., 2009). Although these molecules demonstrate a significant enhancement in trabecular bone, 1D11-mediated TGF-β blockade increases both trabecular bone volume and improves cortical bone strength. These superior skeletal effects may be a result of the complete abrogation of TGF-β signaling through the avid binding and neutralization of all extracellular TGF-β isoforms, compared to the inhibition of intracellular receptor associated enzymes currently targeted by small molecules. These findings clearly illustrate the potential of compounds which can specifically target TGF-β in vivo, and suggest a therapeutic approach to increase bone mass in conditions where excessive bone destruction is prevalent, such as cancer-induced bone disease or osteoporosis.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VII. REFERENCES

The following references, to the extent that they provide exemplary procedural or other details supplementary to those set forth herein, are specifically incorporated herein by reference.

U.S. Pat. No. 4,196,265
U.S. Pat. No. 4,722,948
U.S. Pat. No. 4,843,112
U.S. Pat. No. 4,863,732

U.S. Pat. No. 4,975,526
U.S. Pat. No. 5,571,714
U.S. Pat. No. 5,772,998
U.S. Pat. No. 5,783,185
U.S. Pat. No. 5,085,861
U.S. Pat. No. 5,162,114
U.S. Pat. No. 5,399,363
U.S. Pat. No. 5,466,468
U.S. Pat. No. 5,531,791
U.S. Pat. No. 5,543,158
U.S. Pat. No. 5,580,579
U.S. Pat. No. 5,629,001
U.S. Pat. No. 5,641,515
U.S. Pat. No. 5,741,796
U.S. Pat. No. 5,792,451
U.S. Pat. No. 5,840,290
U.S. Pat. No. 5,972,703
U.S. Pat. No. 6,074,674
U.S. Pat. No. 6,270,750
U.S. Pat. No. 6,281,195
U.S. Pat. No. 6,288,043
U.S. Pat. No. 6,485,754
U.S. Pat. No. 6,537,514
U.S. Pat. No. 6,613,308
U.S. Pat. No. 6,662,805
U.S. Pat. No. 6,936,270
U.S. Pat. No. 7,008,433
Alliston et al., *EMJO. J.*, 20(9):2254-2272, 2001.
Ashton et al., *Bone*, 6:313-319, 1985.
Aubin, *Biochem. Cell Biology*, 76:899-910, 1998.
Balooch et al., *Proc. Natl. Acad. Sci. USA*, 102(52):18813-18818, 2005.
Beamer et al., *Bone*, 18(5):397-403, 1996.
Beidler et al., *J. Immunol.*, 141(11):4053-4060, 1988.
Bleiberg, *Connect Tissue Res.*, 14:121-127, 1985.
Campbell et al., *Am. Rev. Respir. Dis.*, 130(3):417-423, 1984.
Cavo et al., *New England Journal of Medicine* 354:1076-1078, 2006.
Dempster et al., *Endocr. Rev.*, 14(6):690-709, 1993.
EP Application 125,023
EP Application 171,496
EP Application 173,494
EP Application 184,187
Filvaroff et al., *Development*, 126(19):4267-4279, 1999.
Friedenstein et al., *Exp. Hematol.*, 10:217-227, 1982.
Friedenstein et al., *Transplantation*, 6:230-247, 1968.
Gefter et al., *Somatic Cell Genet.*, 3:231-236, 1977.
Goding, In: *Monoclonal Antibodies: Principles and Practice*, 2d ed., Academic Press, Orlando, Fla., pp 60-61, 71-74, 1986.
Gronthos et al., *Blood*, 84:4164-4173, 1994.
Gronthos et al., *J. Bone Min. Res.*, 14:47-56, 1999.
Harlow and Lane, In: *Antibodies: A Laboratory Manual*, Cold Spring Harbor Laboratory, 1988.
Hwang et al., *Crit. Rev. Ther. Drug Carrier Syst.*, 15(3):243-284, 1998.
Itoh et al., *J. Bone Miner res.*, 15(9):1766-1775, 2000.
Jaiswal et al., *J. Biol. Chem.*, 275:9645-9652, 2000.
Jones et al., *Nature*, 321:522-525, 1986.
Kadiyala et al., *Cell Transplantation*, 6:125-134, 1997.
Kale et al., *Nat. Biotech.*, 18:954-958, 2000.
Kang et al., *EMBO. J.*, 24(14):2543-2555, 2005.
Karst et al., *J. Cell Physiol.*, 200:99-106, 2004.
Katagirl et al., *Biochem. Biophys. Res. Commun.*, 172(1):295-299, 1990.
Kohler and Milstein, *Eur. J. Immunol.*, 6:511-519, 1976.
Kohler and Milstein, *Nature*, 256:495-497, 1975.
Lee and Lorenzo, *Endocrinology*, 140(8):3552-3561, 1999.
Lieber et al., *Appl. Spectrosc.* 57:1363-67, 2003.
Long, *J. Clin. Invest.*, 95:881-887, 1995.
Mathiowitz et al., *Nature*, 386(6623):410-414, 1997.
Mohammad et al., *PLoS ONE*, 4:e5275, 2009.
Morrison, *Science*, 229(4719):1202-1207, 1985.
Mundy and Bonewald, *Ann. NY Acad. Sci.*, 593:91-97, 1990.
Oliver & Pharr, *J. Mater. Res.*, 19:3-20, 2004.
PCT Appln. PCT/US86/02269
PCT Appln. WO 86/01533
Petite et al., *Nat. Biotech.*, 18:959-963, 2000.
Phinney et al., *J. Cellular Biochem.*, 75:424-436, 1999.
Pittenger et al., *Science*, 284:143-147, 1999.
Quinn et al., *J. Bone Miner. Res.*, 16:1787-94, 2001.
Raisz, *J. Clin. Invest.*, 115(12):3318-3325, 2005.
Reddi and Huggins, *Proc. Natl. Acad. Sci. USA*, 69:1601-1605, 1972.
Remington's Pharmaceutical Sciences, 15th ed., pages 1035-1038 and 1570-1580, Mack Publishing Company, Easton, Pa., 1980.
Remingtons Pharmaceutical Sciences, 18th Ed. Mack Printing Company, pp. 1289-1329, 1990.
Schriefer et al., *J. Biomech.*, 38:467-75, 2006.
Shaw et al., *J. Natl. Cancer Inst.*, 80(19):1553-1559, 1988.
Sun et al., *J. Steroid Biochem.*, 26(1):83-92, 1987.
Takuwa et al., *Biochem. Biophys. Res. Commun.*, 174(1):96-101, 1991.
Terpos et al., *Annals of Oncology* 16:1223-1231, 2005.
Thirunavukkaraus et al., *J. Biol. Chem.*, 276:36241-50, 2001.
Verhoeyen et al., *Science*, 239(4847):1534-1536, 1988.
Wood et al., *J. Clin. Lab. Immunol.*, 17(4):167-171, 1985.
Zohar et al., *Blood*, 90:3471-3481, 1997.

The invention claimed is:

1. A method of increasing bone growth in a subject comprising administering to said subject an antibody designated as 1D11 and deposited with the American Type Culture Collection as Accession No. HB9849, wherein said antibody is administered systemically or to a bone target site, wherein the subject suffers from one or more conditions selected from the group consisting of bone fracture, a bone reconstruction and/or grafting procedure, a bone segmental defect, periodontal disease, osteolytic bone disease, age-related osteoporosis, osteoporosis associated with post-menopausal hormone status, disuse osteoporosis, diabetes-related osteoporosis, glucocorticoid-related osteoporosis, and vitamin D deficiency, and wherein said subject does not have cancer.

2. The method of claim 1, wherein said antibody is administered to said subject systemically.

3. The method of claim 1, wherein said antibody is administered intravenously, intra-peritoneally, intramuscularly, or subcutaneously.

4. The method of claim 1, wherein said antibody is administered to a bone target site.

5. The method of claim 1, wherein said subject is a human subject.

6. The method of claim 1, wherein the subject does not have primary hyperparathyroidism.

7. The method of claim 1, wherein the subject suffers from one or more conditions selected from the group consisting of bone fracture, a bone reconstruction and/or grafting procedure, a bone segmental defect, periodontal disease, osteolytic bone disease, and vitamin D deficiency.

* * * * *

UNITED STATES PATENT AND TRADEMARK OFFICE
CERTIFICATE OF CORRECTION

| | |
|---|---|
| PATENT NO. | : 11,192,945 B2 |
| APPLICATION NO. | : 14/582631 |
| DATED | : December 7, 2021 |
| INVENTOR(S) | : Edwards et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 61 days.

Signed and Sealed this
Sixth Day of December, 2022

Katherine Kelly Vidal
*Director of the United States Patent and Trademark Office*